(12) United States Patent
Lane et al.

(10) Patent No.: US 7,951,197 B2
(45) Date of Patent: *May 31, 2011

(54) TWO-PIECE PROSTHETIC VALVES WITH SNAP-IN CONNECTION AND METHODS FOR USE

(75) Inventors: Ernest Lane, Huntington Beach, CA (US); Shouyan Lee, Rancho Santa Margarita, CA (US); Charles Huang, Villa Park, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/419,059

(22) Filed: Apr. 6, 2009

(65) Prior Publication Data

US 2009/0192599 A1    Jul. 30, 2009

Related U.S. Application Data

(63) Continuation of application No. 11/279,246, filed on Apr. 10, 2006, now Pat. No. 7,513,909.

(51) Int. Cl.
*A61F 2/24* (2006.01)
(52) U.S. Cl. .......................................................... 623/2.4
(58) Field of Classification Search ..................... 623/2.4
See application file for complete search history.

(56) References Cited

U.S. PATENT DOCUMENTS

| | | |
|---|---|---|
| 3,143,742 A | 8/1964 | Cromie |
| 3,320,974 A | 5/1967 | High et al. |
| 3,370,305 A | 2/1968 | Goott et al. |
| 3,371,352 A | 3/1968 | Siposs |
| 3,409,013 A | 11/1968 | Berry |
| 3,464,065 A | 9/1969 | Cromie |
| 3,546,710 A | 12/1970 | Ivanovich et al. |
| 3,571,815 A | 3/1971 | Somyk |
| 3,574,865 A | 4/1971 | Hamaker |
| 3,628,535 A | 12/1971 | Ostrowsky et al. |

(Continued)

FOREIGN PATENT DOCUMENTS

CN    2356656    1/2000

(Continued)

OTHER PUBLICATIONS

Lutter, et al., Percutaneous Valve Replacement: Current State and Future Prospects; Ann. Thorac. Surg. 2004;78:2199-2206.

(Continued)

*Primary Examiner* — Bruce E Snow
(74) *Attorney, Agent, or Firm* — Katrina A. Witschen; Mike Jaro

(57) ABSTRACT

A prosthetic heart valve assembly includes a gasket member and a valve member including a plurality of fasteners and a plurality of engagement members corresponding to the fasteners. The fasteners and/or engagement members may be configured to guide the engagement members into engagement with the fasteners. For example, the fasteners may include U-shaped spring-biased clips, e.g., attached to a core or other portion of a sewing cuff of the gasket member, and the engagement members may include latches or barbed protrusions that engage one or more holes in the fasteners. During use, the gasket member is introduced into a tissue annulus, and secured to the annulus, e.g., using a plurality of clips directed through the sewing cuff. The valve member is then introduced into the annulus and the engagement members are snapped or otherwise guided into engagement with the fasteners to secure the valve member relative to the gasket member.

12 Claims, 13 Drawing Sheets

U.S. PATENT DOCUMENTS

| | | |
|---|---|---|
| 3,686,740 A | 8/1972 | Shiley |
| 3,691,567 A | 9/1972 | Cromie |
| 3,710,744 A | 1/1973 | Goodenough et al. |
| 3,744,060 A | 7/1973 | Bellhouse et al. |
| 3,755,823 A | 9/1973 | Hancock |
| 3,800,403 A | 4/1974 | Anderson |
| 3,839,741 A | 10/1974 | Haller |
| 3,959,827 A | 6/1976 | Kaster |
| 3,974,854 A | 8/1976 | Kurpanek |
| 3,996,623 A | 12/1976 | Kaster |
| 3,997,923 A | 12/1976 | Possis |
| 4,035,849 A | 7/1977 | Angell et al. |
| 4,078,268 A | 3/1978 | Possis |
| 4,078,468 A | 3/1978 | Civitello |
| 4,084,268 A | 4/1978 | Ionexcu et al. |
| 4,106,129 A | 8/1978 | Carpentier et al. |
| 4,164,046 A | 8/1979 | Cooley |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,683,883 A | 8/1987 | Martin |
| 4,687,483 A | 8/1987 | Fisher et al. |
| 4,692,164 A | 9/1987 | Dzemeshkevich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,914,097 A | 4/1990 | Proudian et al. |
| 4,917,698 A | 4/1990 | Carpentier et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,708 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,346 A | 3/1995 | Walker et al. |
| 5,397,348 A | 3/1995 | Campbell et al. |
| 5,397,351 A | 3/1995 | Pavcnik et al. |
| 5,406,857 A | 4/1995 | Eberhardt et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A | 8/1996 | Vesely et al. |
| 5,549,666 A | 8/1996 | Hata et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov |
| 5,578,076 A | 11/1996 | Krueger et al. |
| 5,584,803 A | 12/1996 | Stevens et al. |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,662,704 A | 9/1997 | Gross |
| 5,669,917 A | 9/1997 | Sauer |
| 5,693,090 A | 12/1997 | Unsworth et al. |
| 5,695,503 A | 12/1997 | Krueger et al. |
| 5,713,952 A | 2/1998 | Vanney et al. |
| 5,713,953 A | 2/1998 | Vallana et al. |
| 5,716,370 A | 2/1998 | Williamson, IV et al. |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |
| 5,824,060 A | 10/1998 | Christie et al. |
| 5,824,061 A | 10/1998 | Quijano et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,603 A | 1/1999 | Reif |
| 5,860,992 A | 1/1999 | Daniel |
| 5,861,028 A | 1/1999 | Angell |
| 5,865,801 A | 2/1999 | Houser |
| 5,876,436 A | 3/1999 | Vanney et al. |
| 5,879,371 A | 3/1999 | Gardiner et al. |

| Patent | Date | Inventor(s) |
|---|---|---|
| 5,891,160 A | 4/1999 | Williamson, IV et al. |
| 5,891,195 A | 4/1999 | Klostermeyer et al. |
| 5,895,420 A | 4/1999 | Mirsch, II et al. |
| 5,902,308 A | 5/1999 | Murphy |
| 5,908,450 A | 6/1999 | Gross et al. |
| 5,908,452 A | 6/1999 | Bokros et al. |
| 5,910,170 A | 6/1999 | Reimink et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,969 A | 8/1999 | Carpentier et al. |
| 5,935,163 A | 8/1999 | Gabbay |
| 5,957,949 A | 9/1999 | Leonhardt et al. |
| 5,961,549 A | 10/1999 | Nguyen et al. |
| 5,961,550 A | 10/1999 | Carpentier |
| 5,972,004 A | 10/1999 | Williamson, IV et al. |
| 5,972,024 A | 10/1999 | Northrup, III |
| 5,976,183 A | 11/1999 | Ritz |
| 5,984,959 A | 11/1999 | Robertson et al. |
| 5,984,973 A | 11/1999 | Girard et al. |
| 6,007,577 A | 12/1999 | Vanney et al. |
| 6,010,531 A | 1/2000 | Donlon et al. |
| 6,042,607 A | 3/2000 | Williamson, IV et al. |
| 6,045,576 A | 4/2000 | Starr et al. |
| 6,059,827 A | 5/2000 | Fenton, Jr. |
| 6,066,160 A | 5/2000 | Colvin et al. |
| 6,068,657 A | 5/2000 | Lapeyre et al. |
| 6,074,041 A | 6/2000 | Gardiner et al. |
| 6,074,417 A | 6/2000 | Peredo |
| 6,074,418 A | 6/2000 | Buchanan et al. |
| 6,081,737 A | 6/2000 | Shah |
| 6,083,179 A | 7/2000 | Oredsson |
| 6,096,074 A | 8/2000 | Pedros |
| 6,099,475 A | 8/2000 | Seward et al. |
| 6,102,944 A | 8/2000 | Huynh |
| 6,106,550 A | 8/2000 | Magovern et al. |
| 6,110,200 A | 8/2000 | Hinnenkamp |
| 6,113,632 A | 9/2000 | Reif |
| 6,117,091 A | 9/2000 | Young et al. |
| 6,126,007 A | 10/2000 | Kari et al. |
| 6,129,758 A | 10/2000 | Love |
| 6,139,575 A | 10/2000 | Shu et al. |
| 6,143,024 A | 11/2000 | Campbell et al. |
| 6,143,025 A | 11/2000 | Stobie et al. |
| 6,149,658 A | 11/2000 | Gardiner et al. |
| 6,162,233 A | 12/2000 | Williamson, IV et al. |
| 6,165,183 A | 12/2000 | Kuehn et al. |
| 6,168,614 B1 | 1/2001 | Andersen et al. |
| 6,176,877 B1 | 1/2001 | Buchanan et al. |
| 6,183,512 B1 | 2/2001 | Hawanec, Jr. et al. |
| 6,197,054 B1 | 3/2001 | Hamblin, Jr. et al. |
| 6,200,306 B1 | 3/2001 | Klostermeyer |
| 6,203,553 B1 | 3/2001 | Robertson |
| 6,214,043 B1 | 4/2001 | Krueger et al. |
| 6,217,610 B1 | 4/2001 | Carpentier et al. |
| 6,217,611 B1 | 4/2001 | Klostermeyer |
| 6,231,561 B1 | 5/2001 | Frazier et al. |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,245,105 B1 | 6/2001 | Nguyen et al. |
| 6,254,636 B1 | 7/2001 | Peredo |
| 6,264,691 B1 | 7/2001 | Gabbay |
| 6,270,526 B1 | 8/2001 | Cox |
| 6,270,527 B1 | 8/2001 | Campbell et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,290,674 B1 | 9/2001 | Roue et al. |
| 6,299,638 B1 | 10/2001 | Sauter |
| 6,309,417 B1 | 10/2001 | Spence |
| 6,312,447 B1 | 11/2001 | Grimes |
| 6,312,465 B1 | 11/2001 | Griffin et al. |
| 6,319,280 B1 | 11/2001 | Schoon |
| 6,319,281 B1 | 11/2001 | Patel |
| 6,322,588 B1 | 11/2001 | Ogle et al. |
| 6,328,727 B1 | 12/2001 | Frazier et al. |
| 6,328,763 B1 | 12/2001 | Love et al. |
| 6,338,740 B1 | 1/2002 | Carpentier |
| 6,350,281 B1 | 2/2002 | Rhee |
| 6,358,278 B1 | 3/2002 | Brendzel et al. |
| 6,358,556 B1 | 3/2002 | Ding et al. |
| 6,371,983 B1 | 4/2002 | Lane |
| 6,391,053 B1 | 5/2002 | Brendzel et al. |
| 6,395,025 B1 | 5/2002 | Fordenbacher et al. |
| 6,402,780 B2 | 6/2002 | Williamson, IV et al. |
| 6,409,759 B1 | 6/2002 | Peredo |
| 6,413,275 B1 | 7/2002 | Nguyen et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,447,524 B1 | 9/2002 | Knodel |
| 6,454,799 B1 | 9/2002 | Schreck |
| 6,458,153 B1 | 10/2002 | Bailey et al. |
| 6,461,382 B1 | 10/2002 | Cao |
| 6,468,305 B1 | 10/2002 | Otte |
| 6,503,272 B2 | 1/2003 | Duerig et al. |
| 6,514,265 B2 | 2/2003 | Ho et al. |
| 6,530,952 B2 | 3/2003 | Vesely |
| 6,547,827 B2 | 4/2003 | Carpentier et al. |
| 6,551,332 B1 | 4/2003 | Nguyen et al. |
| 6,558,418 B2 | 5/2003 | Carpentier et al. |
| 6,569,196 B1 | 5/2003 | Vesely |
| 6,582,462 B1 | 6/2003 | Anderson et al. |
| 6,585,766 B1 | 7/2003 | Huynh et al. |
| 6,589,279 B1 | 7/2003 | Anderson et al. |
| 6,598,307 B2 | 7/2003 | Love et al. |
| 6,602,289 B1 | 8/2003 | Colvin et al. |
| 6,607,541 B1 | 8/2003 | Gardiner et al. |
| 6,613,059 B2 | 9/2003 | Ho et al. |
| 6,613,085 B1 | 9/2003 | Anderson et al. |
| 6,641,593 B1 | 11/2003 | Schaller et al. |
| 6,652,578 B2 | 11/2003 | Bailey et al. |
| 6,676,671 B2 | 1/2004 | Robertson et al. |
| 6,678,862 B1 | 1/2004 | Love et al. |
| 6,682,559 B2 | 1/2004 | Myers et al. |
| 6,685,739 B2 | 2/2004 | DiMatteo et al. |
| 6,692,513 B2 | 2/2004 | Streeter et al. |
| 6,695,859 B1 | 2/2004 | Golden et al. |
| 6,709,457 B1 | 2/2004 | Otte et al. |
| 6,716,243 B1 | 4/2004 | Colvin et al. |
| 6,716,244 B2 | 4/2004 | Klaco |
| 6,716,789 B1 | 4/2004 | Cox |
| 6,719,790 B2 | 4/2004 | Brendzel et al. |
| 6,730,118 B2 | 5/2004 | Spenser et al. |
| 6,733,525 B2 | 5/2004 | Yang |
| 6,764,508 B1 | 7/2004 | Roehe et al. |
| 6,767,362 B2 | 7/2004 | Schreck |
| 6,769,434 B2 | 8/2004 | Liddicoat et al. |
| 6,776,785 B1 | 8/2004 | Yencho |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,830,585 B1 | 12/2004 | Artof et al. |
| 6,833,924 B2 | 12/2004 | Love et al. |
| 6,846,324 B2 | 1/2005 | Stobie |
| 6,846,325 B2 | 1/2005 | Liddicoat |
| 6,873,902 B1 | 1/2005 | Nguyen et al. |
| 6,872,226 B2 | 3/2005 | Cali et al. |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,908,481 B2 | 6/2005 | Cribier |
| 6,911,043 B2 | 6/2005 | Myers et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,929,653 B2 | 8/2005 | Streeter |
| 6,939,365 B1 | 9/2005 | Fogarty |
| 6,945,980 B2 | 9/2005 | Nguyen et al. |
| 6,945,997 B2 | 9/2005 | Huynh et al. |
| 6,960,221 B2 | 11/2005 | Ho et al. |
| 6,974,476 B2 | 12/2005 | McGuckin et al. |
| 7,011,681 B2 | 3/2006 | Vesely |

| | | |
|---|---|---|
| 7,025,780 B2 | 4/2006 | Gabbay |
| 7,037,333 B2 | 5/2006 | Myers et al. |
| 7,070,616 B2 | 7/2006 | Majercak et al. |
| 7,083,648 B2 | 8/2006 | Yu |
| 7,097,659 B2 | 8/2006 | Woolfson et al. |
| 7,101,396 B2 | 9/2006 | Artof et al. |
| 7,134,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 | 2/2007 | Hill et al. |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,445,632 B2 | 11/2008 | McGuckin et al. |
| 7,513,909 B2 | 4/2009 | Lane et al. |
| 7,547,313 B2 | 5/2009 | Gardiner et al. |
| 7,556,647 B2 | 7/2009 | Drews et al. |
| 7,578,843 B2 | 8/2009 | Shu |
| 7,597,711 B2 | 10/2009 | Drews et al. |
| 7,708,775 B2 | 5/2010 | Rowe et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat et al. |
| 7,803,184 B2 | 9/2010 | McGuckin et al. |
| 2001/0018592 A1 | 4/2001 | Schaller et al. |
| 2001/0007956 A1 | 7/2001 | Letac et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 | 6/2002 | Schwartz |
| 2002/0077698 A1 | 6/2002 | Peredo |
| 2002/0091441 A1 | 7/2002 | Nguyen et al. |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Bonhoeffer et al. |
| 2003/0036795 A1 | 2/2003 | Andersen et al. |
| 2003/0040792 A1 | 2/2003 | Gabbay |
| 2003/0045902 A1 | 3/2003 | Weadeock |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 9/2003 | Nguyen et al. |
| 2003/0199963 A1 | 10/2003 | Tower et al. |
| 2003/0199971 A1 | 10/2003 | Tower et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 | 3/2004 | Woolfson |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0122514 A1 | 6/2004 | Fogarty |
| 2004/0122516 A1 | 6/2004 | Fogarty |
| 2004/0122526 A1 | 6/2004 | Imran |
| 2004/0167573 A1 | 8/2004 | Williamson, IV et al. |
| 2004/0167620 A1 | 8/2004 | Ortiz et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |

| | | |
|---|---|---|
| 2005/0165477 A1 | 7/2005 | Andruiza et al. |
| 2005/0165479 A1 | 7/2005 | Lane |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234545 A1 | 10/2005 | Nugent et al. |
| 2005/0234546 A1 | 10/2005 | Nuget et al. |
| 2005/0240259 A1 | 10/2005 | Sisken et al. |
| 2005/0240263 A1 | 10/2005 | Fogarty |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004389 A1 | 1/2006 | Nguyen et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1* | 5/2006 | Chinn et al. .......... 623/2.4 |
| 2006/0122634 A1 | 6/2006 | Ino |
| 2006/0122692 A1 | 6/2006 | Gilad et al. |
| 2006/0135964 A1 | 6/2006 | Vesely |
| 2006/0136052 A1 | 6/2006 | Vesely |
| 2006/0136054 A1 | 6/2006 | Berg et al. |
| 2006/0149360 A1 | 7/2006 | Schwammenthal et al. |
| 2006/0149367 A1 | 7/2006 | Sieracki |
| 2006/0154230 A1 | 7/2006 | Cunanan |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane |
| 2006/0195185 A1 | 8/2006 | Lane |
| 2006/0195186 A1 | 8/2006 | Drews |
| 2006/0207031 A1 | 9/2006 | Cunanan et al. |
| 2006/0229708 A1 | 10/2006 | Powell et al. |
| 2006/0235508 A1 | 10/2006 | Lane |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woofson et al. |
| 2006/0276888 A1 | 12/2006 | Lee |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010835 A1 | 1/2007 | Breton et al. |
| 2007/0010876 A1 | 1/2007 | Salahieh et al. |
| 2007/0010877 A1 | 1/2007 | Salahieh et al. |
| 2007/0016285 A1 | 1/2007 | Lane |
| 2007/0016286 A1 | 1/2007 | Herrmann et al. |
| 2007/0016288 A1 | 1/2007 | Gurskis |
| 2007/0027461 A1 | 2/2007 | Gardiner et al. |
| 2007/0043435 A1 | 2/2007 | Seguin et al. |
| 2007/0142848 A1 | 2/2007 | Ainsworth et al. |
| 2007/0078509 A1 | 4/2007 | Lotfy |
| 2007/0078510 A1 | 4/2007 | Ryan |
| 2007/0095698 A1 | 5/2007 | Cambron |
| 2007/0100440 A1 | 5/2007 | Figulla et al. |
| 2007/0106313 A1 | 5/2007 | Golden et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0004696 A1 | 1/2008 | Vesely |
| 2008/0033543 A1 | 2/2008 | Gurskis et al. |
| 2008/0071361 A1 | 3/2008 | Tuval et al. |
| 2008/0071369 A1 | 3/2008 | Tuval et al. |
| 2008/0097595 A1 | 4/2008 | Gabbay |
| 2008/0119875 A1 | 5/2008 | Ino et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0112233 A1 | 4/2009 | Xiao |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0210052 A1 | 8/2009 | Powell et al. |
| 2009/0264903 A1 | 10/2009 | Lee et al. |
| 2009/0319038 A1 | 12/2009 | Gurskis et al. |
| 2010/0030244 A1 | 2/2010 | Woolfson et al. |
| 2010/0044410 A1 | 2/2010 | Argentine et al. |
| 2010/0100174 A1 | 4/2010 | Gurskis |
| 2010/0249894 A1 | 9/2010 | Oba et al. |

FOREIGN PATENT DOCUMENTS

| | | |
|---|---|---|
| DE | 19532973 | 11/1996 |
| EP | 0 084 395 | 8/1986 |
| EP | 0 096 721 | 12/1987 |
| EP | 0 125 393 | 12/1987 |
| EP | 0 179 562 | 7/1989 |
| EP | 1057460 | 12/2000 |
| EP | 1 088 529 | 4/2001 |
| EP | 1171059 | 1/2002 |
| EP | 971 650 | 1/2005 |
| EP | 171 059 | 2/2005 |
| GB | 1093599 | 12/1967 |
| GB | 1477643 | 6/1977 |
| GB | 2011259 | 7/1979 |
| GB | 2 056 023 | 3/1981 |
| GB | 2 069 843 | 9/1981 |
| GB | 2254254 | 10/1992 |
| GB | 2 279 134 | 12/1994 |
| SU | 1116573 | 7/1985 |
| WO | 87/05489 | 9/1987 |
| WO | 89/00084 | 2/1989 |
| WO | 91/15167 | 10/1991 |
| WO | 92/01269 | 8/1992 |
| WO | 92/13502 | 8/1992 |
| WO | 92/19184 | 11/1992 |
| WO | 92/19185 | 11/1992 |
| WO | 95/17139 | 6/1995 |
| WO | 95/28899 | 11/1995 |
| WO | 96/40006 | 12/1996 |
| WO | 97/09933 | 3/1997 |
| WO | 97/09944 | 3/1997 |
| WO | 97/27799 | 8/1997 |
| WO | 97/41801 | 11/1997 |
| WO | 97/42871 | 11/1997 |
| WO | 98/06329 | 2/1998 |
| WO | 99/11201 | 3/1999 |
| WO | 99/15112 | 4/1999 |
| WO | 99/51169 | 10/1999 |
| WO | 00/32105 | 6/2000 |
| WO | 00/40176 | 7/2000 |

| | | |
|---|---|---|
| WO | 00/44311 | 8/2000 |
| WO | 00/56250 | 9/2000 |
| WO | 00/59382 | 10/2000 |
| WO | 00/60995 | 10/2000 |
| WO | 00/64380 | 11/2000 |
| WO | 01/10310 | 2/2001 |
| WO | 01/10312 | 2/2001 |
| WO | 01/58363 | 8/2001 |
| WO | 01/76510 | 10/2001 |
| WO | 01/82840 | 11/2001 |
| WO | 01/87190 | 11/2001 |
| WO | 2004/006810 | 1/2004 |
| WO | 2004/089246 | 10/2004 |
| WO | 2005/004753 | 1/2005 |
| WO | 2005/020842 | 3/2005 |
| WO | 2005/039452 | 5/2005 |
| WO | 2005/072655 | 8/2005 |
| WO | 2006/086135 | 8/2006 |
| WO | 2009/137517 | 11/2009 |

OTHER PUBLICATIONS

Jansen, et al., "Detachable Shape-Memory Sewing Ring for Heart Valves," Artif. Organs. vol. 16, No. 3, 1992, pp. 294-297, Helmholtz Institute for Biomedical Engineering, Technical University of Aachen, Aachn, Germany.

* cited by examiner

TWO-PIECE PROSTHETIC VALVES WITH SNAP-IN CONNECTION AND METHODS FOR USE

The present application is a continuation of application Ser. No. 11/279,246, filed Apr. 10, 2006, issuing as U.S. Pat. No. 7,513,909 on Apr. 7, 2009, which claims benefit of provisional application Ser. No. 60/669,704, filed Apr. 8, 2005, the entire disclosure of which is expressly incorporated by reference herein.

FIELD OF THE INVENTION

The present invention generally relates to prosthetic valves, and, more particularly, relates to two-piece prosthetic valves, and to methods for making and using them.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuting the sewing ring down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

SUMMARY

The present invention is directed generally to prosthetic valves, and, more particularly, to two-piece prosthetic valves, and to methods for making and using them.

In accordance with one embodiment, a prosthetic heart valve assembly is provided that includes a gasket member and a valve member including a plurality of fasteners and a plurality of engagement members corresponding to the fasteners. The fasteners and/or engagement members may be configured to guide the engagement members into engagement with the fasteners. For example, the engagement members may include ramped first edges and blunt second edges and the fasteners may define pockets for receiving the engagement members, the ramped edges guiding the engagement members into the pockets and the blunt edges preventing subsequent removal of the engagement members from the fasteners.

In an exemplary embodiment, the fasteners may include U-shaped spring-biased clips, and the engagement members may include latches or barbed protrusions that engage one or more holes or in the clips. For example, the fasteners may be attached to a core or other portion of a sewing cuff of the gasket member, and the engagement members may be integrally formed as part of a frame of the valve member.

In accordance with another embodiment, a method is provided for implanting a prosthetic valve assembly within a tissue annulus, e.g., adjacent or within a site of a native valve, such as a aortic valve annulus. A gasket member may be introduced into the annulus and secured to tissue surrounding the annulus, e.g., using a plurality of clips or other fasteners. A valve member may then be introduced into the annulus and directed towards the gasket member. The gasket member and valve member may include corresponding engagement members and fasteners for securing the valve member relative to the gasket member.

In an exemplary embodiment, the fasteners on one of the gasket member and the valve member may be configured for guiding the fasteners on the other of the gasket member and the valve member as valve member is directed towards the gasket member. For example, the fasteners may include clips or other receptacles and the engagement members may include ramped and blunt edges. As the valve member is directed towards the gasket member, the ramped edges may slidable along the fasteners until the engagement members are engaged with the fasteners. The blunt edges may prevent subsequent removal of the engagement members from the fasteners, thereby securing the valve member relative to the gasket member.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION

Figure 1:
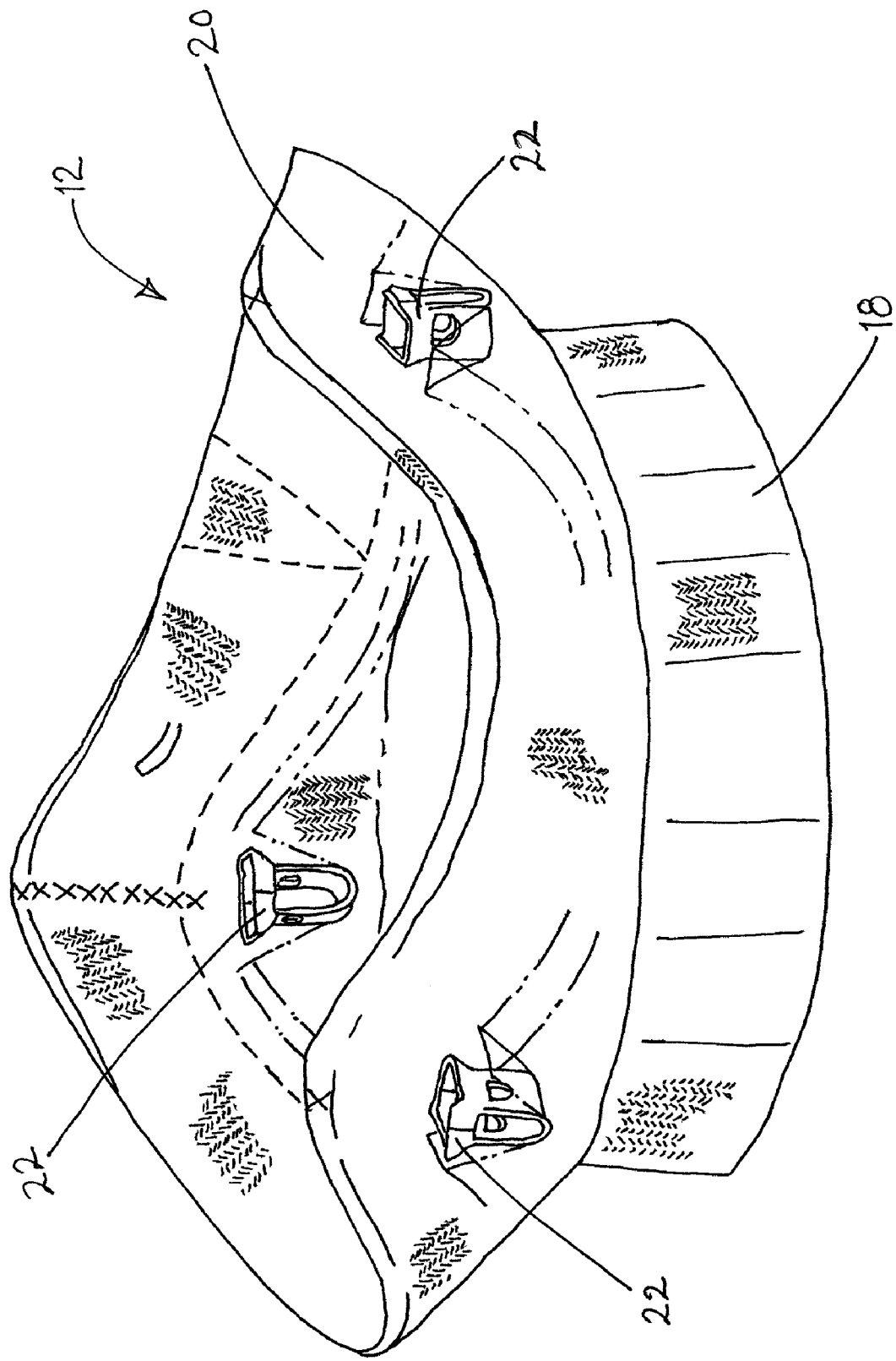
FIG. 1 is a perspective view of a gasket member including three fasteners.
Figure 2:
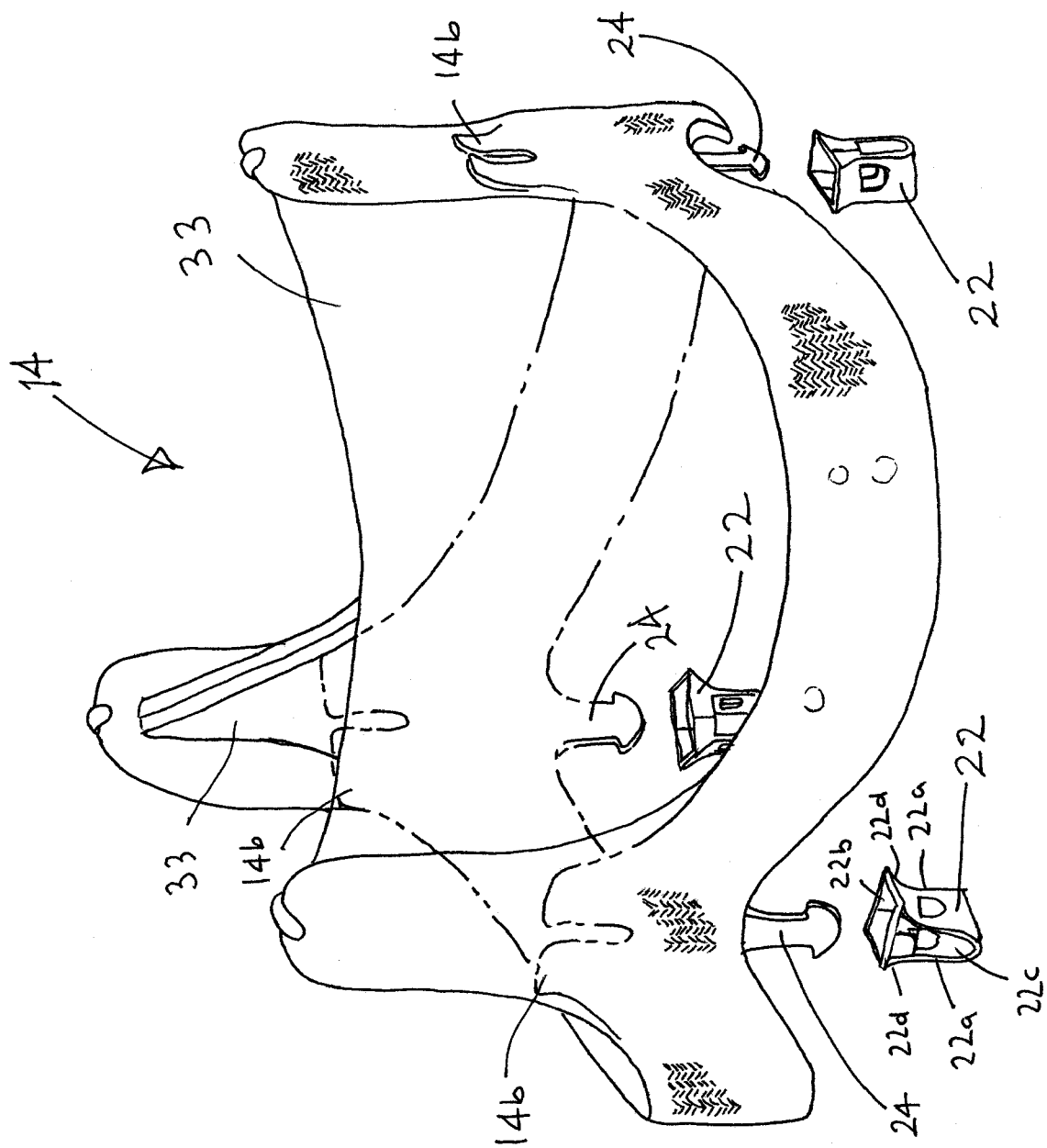
FIG. 2 is a perspective view of a crown or valve member including fasteners for engaging with the fasteners in the gasket member of FIG. 1.
Figure 3:
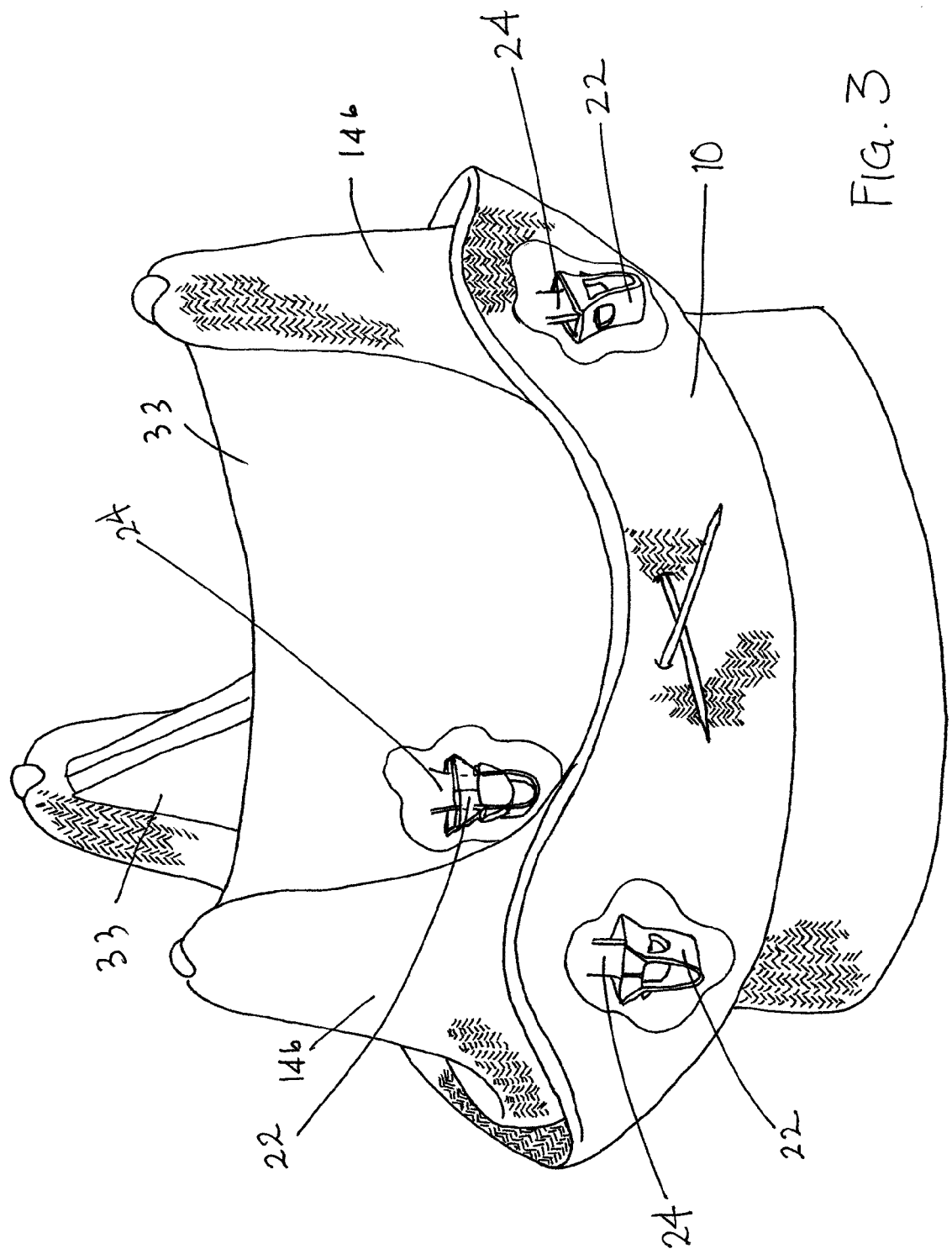
FIG. 3 is a perspective view of the valve member of FIG. 2 secured to the gasket member of FIG. 1, to provide an assembled heart valve assembly.

Turning to the drawings, FIGS. 1-3 show an exemplary embodiment of a heart valve assembly 10 that generally includes a base or gasket member 12 (best seen in FIG. 1) and a crown or valve member or 14 (best seen in FIG. 2). The gasket member 12 is generally an annular shaped body, which may have a substantially circular or noncircular shape, such as a multiple lobular shape. The gasket member 12 and valve member 14 include a plurality of fasteners 22 and engagement members 24, e.g., in corresponding sets, as explained further below.

In one embodiment, as shown in FIG. 1, the gasket member 12 may have a lower portion having a substantially circular shape, and an upper or outer portion having a multiple lobular shape, e.g., a tri-lobular shape (i.e., including three lobes separated by cusps or scallops). The shape may correspond generally to a cross-section of a biological annulus within which the gasket member 12 may be implanted. It will be appreciated that the gasket member 12 may define other noncircular shapes that may correspond to the anatomy of a patient within which the heart valve assembly 10 is to be implanted.

The gasket member 12 may include an annular ring or frame 18 and a flexible cuff or sewing ring 20 that may extend radially outwardly around a periphery of the annular ring 18. Optionally, the gasket member 12 may include other components, e.g., a stand-off or collar (not shown), such as those disclosed in application Ser. Nos. 60/685,265, filed May 27, 2005, and 60/743,185, filed Jan. 27, 2006, the entire disclosures of which are expressly incorporated by reference herein.

The annular ring 18 may be substantially rigid, e.g., retaining its shape, or semi-rigid, e.g., such that the annular ring 18 may be resiliently deformed, e.g., to conform at least partially to the anatomy within which the gasket member 12 is implanted. In addition or alternatively, the annular ring 18 may be elastically or super-elastically deformable, e.g., compressible from its relaxed, expanded configuration into a lower profile configuration, yet resiliently biased to return to the expanded configuration shown when released.

In another alternative, the annular ring 18 may be formed from a shape memory material, e.g., Nitinol, having the expanded configuration heat treated or otherwise programmed into the material. For example, the material of the annular ring 18 may undergo substantial martensitic transformation, e.g., when cooled to a temperature approaching zero degrees Celsius (0° C.), wherein the gasket member 12 may be substantially soft and plastically deformable. When warmed, the material may complete austenitic transformation, e.g., at a temperature below 98° C., such that the gasket member 12 "remembers" its original expanded configuration, and becomes resiliently biased towards the expanded configuration expand from the lower profile configuration. Thus, the gasket member 12 may be cooled to transform the annular ring 18 to a substantially martensitic state to facilitate radial compression of the gasket member 12 for delivery, and warmed, e.g., when exposed to body temperature of a patient, to a substantially austenitic state whereupon the gasket member 12 may become biased to resiliently return towards its original expanded condition upon being released at an implantation site.

Figure 7:
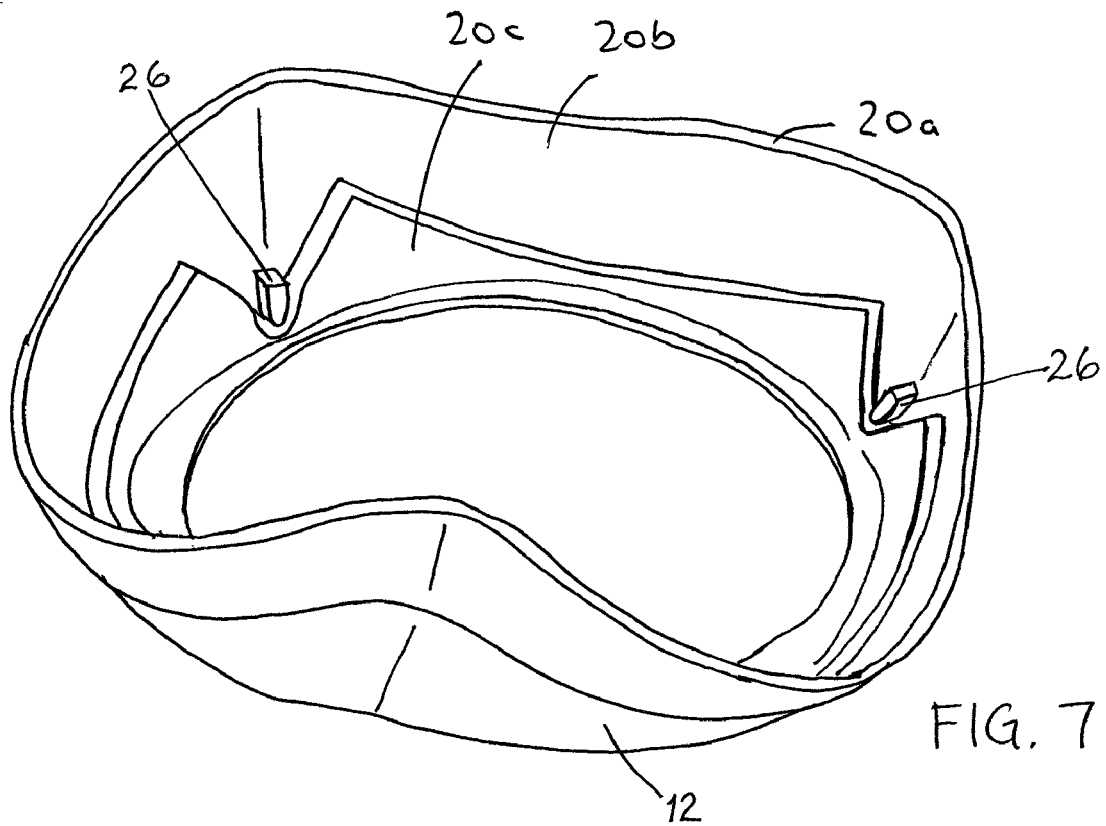
FIGS. 7 and 8 are perspective views of a flexible core for a sewing cuff that may be included in the gasket member of FIG. 4, shown before and after attaching fasteners to the core.
Figure 8:
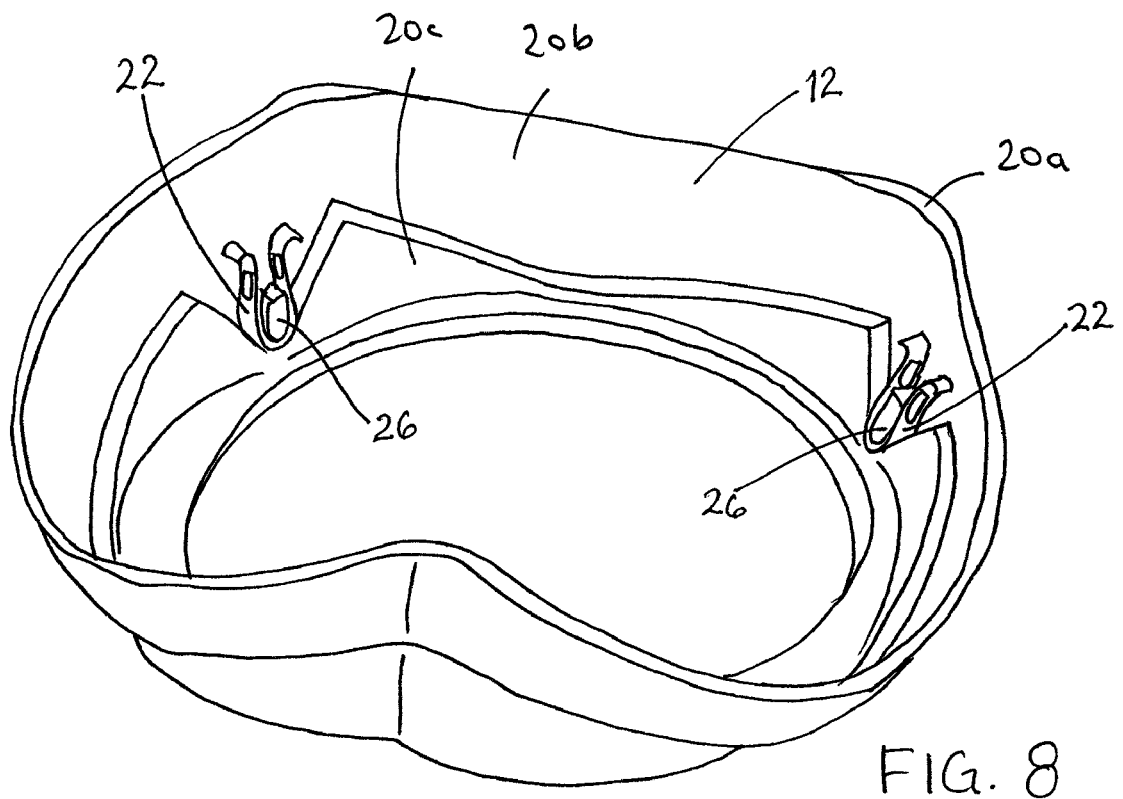

Turning to FIGS. 7 and 8, the cuff 20 generally includes a flexible core 20a, which may be at least partially covered by fabric (not shown, see, e.g., FIG. 1). In exemplary embodiments, the core 20a may be formed from resiliently flexible material, such as silicone or other elastomeric materials. The core 20a may be solid or may include a lattice. Alternatively, the cuff 20 may simply be one or more layers of fabric or other material extending from and/or covering at least a portion of the annular ring 18.

Figure 4:
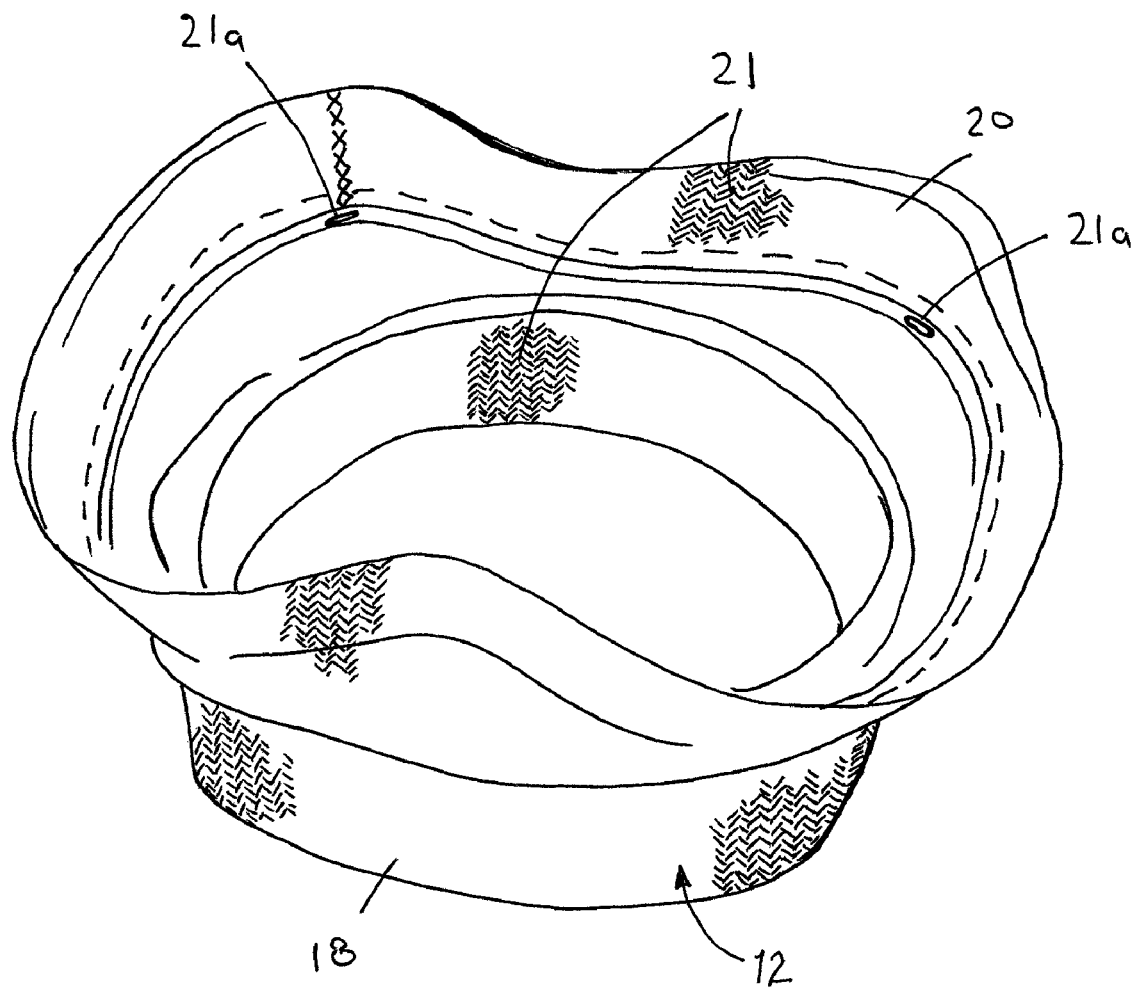
FIG. 4 is a perspective view of a gasket member including a cloth covering overlying a flexible core and annular ring.

In addition, a layer of fabric (not shown) may cover all or a portion of core 20a and/or the annular ring 18, e.g., other than any connectors and/or bearing surfaces, e.g., for securing the valve member 14 to the gasket member 12, as described further elsewhere herein. For example, FIG. 4 shows a layer of fabric 21 substantially covering the components of the gasket member 12. As shown, the fabric covering 21 includes a plurality of holes 21a (e.g., button holes), which may be disposed above or otherwise adjacent the fasteners 22 (not shown in FIG. 4; see, e.g., FIG. 1).

The annular ring 18 and cuff 20 may be integrally formed as a single component or may be separate components attached to one another. In addition, the cuff 20 may be slidably or fixedly attached to the annular ring 18. Additional information on exemplary gasket members and methods for making and using them are disclosed in co-pending application Ser. No. 11/069,081, filed Feb. 28, 2005, the entire disclosure of which is expressly incorporation by reference herein.

Figure 2A:
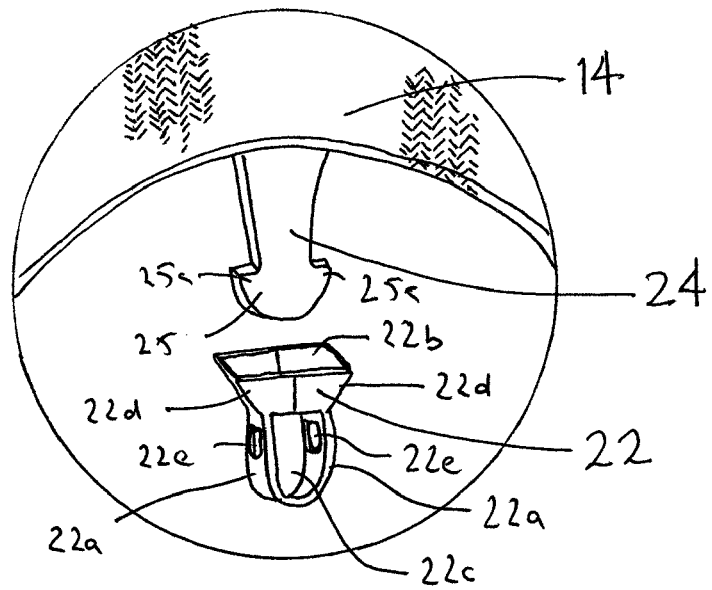
FIGS. 2A-2C are details showing the engagement of one set of the fasteners shown in FIGS. 1 and 2.
Figure 2B:
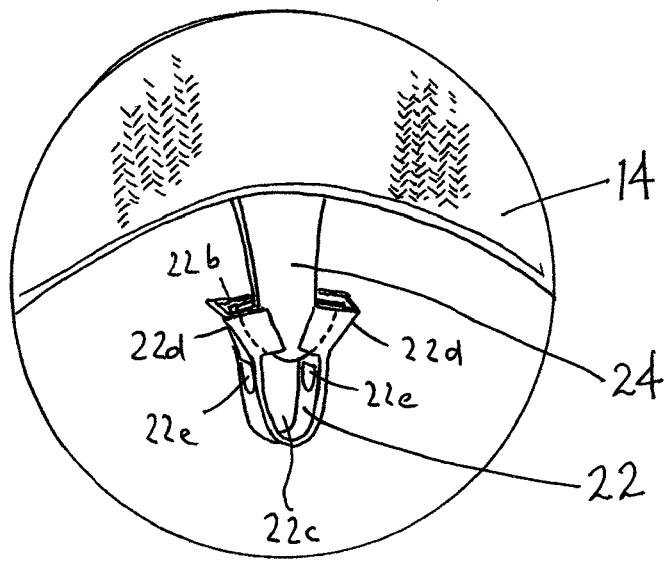
Figure 2C:
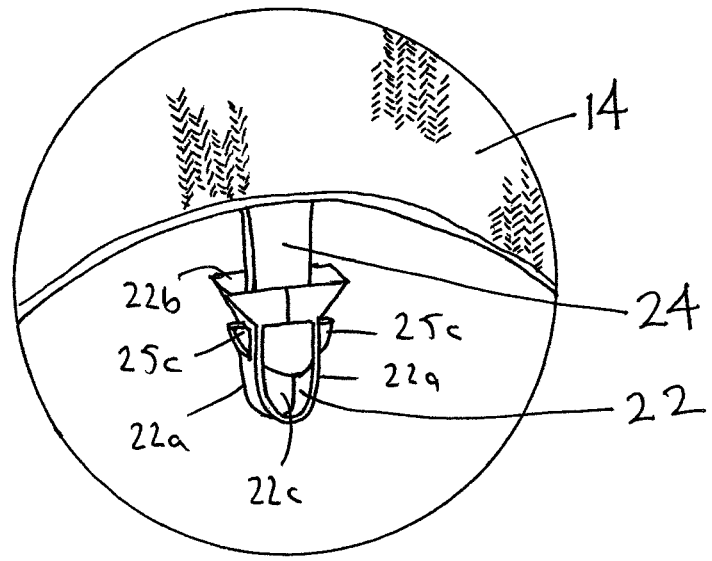

Referring back to FIG. 1, the gasket member 12 includes a plurality of fasteners or receivers 22 for receiving or otherwise engaging engagement members 24 on the valve member 14, e.g., as shown in FIGS. 2A-2C and described further below. The fasteners 22 may be formed as spring-biased clips, for example, as shown in FIGS. 1, 2, 3, 8, 10, 11, 15, and 16. As shown, the gasket member 12 includes three such fasteners 22, e.g., which may be attached at locations corresponding to the commissures of the valve member 14 (and, consequently, the commissures of the tissue annulus within which the gasket member 12 is implanted, as described further below). Alternatively, if desired, the gasket member 12 may include more or fewer fasteners 22 than shown.

Figures 10, 11:
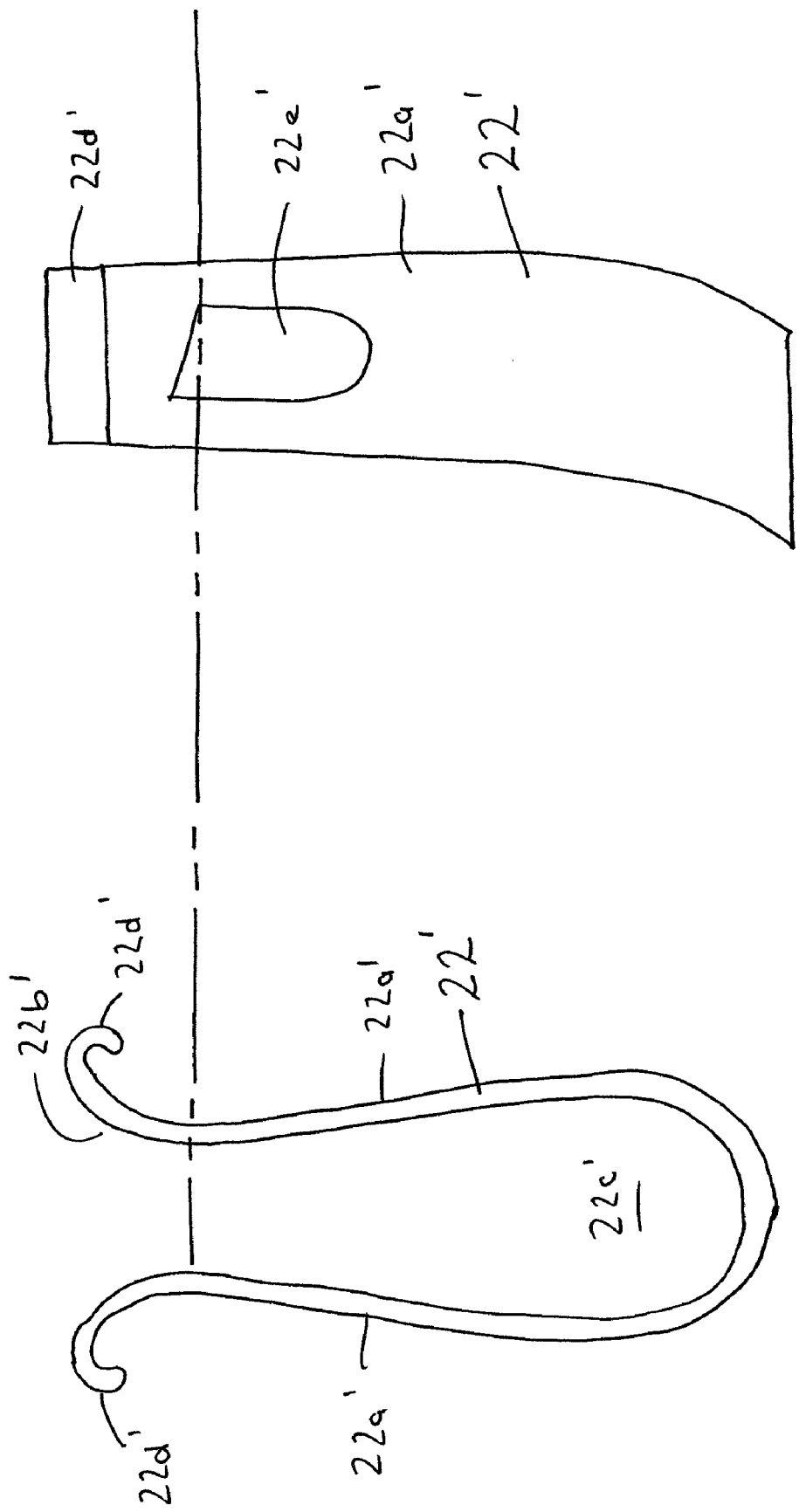
FIGS. 10 and 11 are front and side views, respectively, of a U-shaped spring-biased clip fastener.

Turning to FIGS. 2-2C, a first embodiment of a fastener 22 is shown, namely a "U" shaped clip that includes a pair of spaced-apart legs 22a defining a funnel-shaped opening 22b and a pocket 22c therebetween. Ends 22d of the opposing legs 22a may be bent away from one another and/or may include front and/or rear surfaces defining the opening 22b, e.g., such that the opening 22b has a larger cross-section than the pocket 22c. Alternatively, the legs 22a may have other shapes and/or configurations. For example, as shown in FIGS. 10 and 11, the legs 22a' may extend generally parallel to one another. Ends 22d' of the legs 22a' may curve outwardly, e.g., to provide rounded surfaces adjacent the opening 22b.' Thus, the ends 22d, 22d' may provide tapered and/or rounded surfaces, which may guide or otherwise facilitate receiving the engagement members 24 (not shown), as explained further below.

In addition, the embodiments shown in FIGS. 2-2C and 10-11, the fasteners 22, 22' include holes or slots 22e, 22e,' e.g., in each leg 22a, 22a' and/or otherwise adjacent the pocket 22c, 22c.' The holes 22e may have upper edges that extend substantially perpendicular to the legs 22a, as shown in FIG. 2, or, alternatively, the holes 22e' may have upper edges that are angled, as shown in FIG. 11. Angled upper edges of the holes 22e' may further guide engagement members 24 (not shown; see, e.g., FIG. 15) into the pocket 22c' and/or bias the engagement members 24 towards one side of the fasteners 22.'

Figure 12:
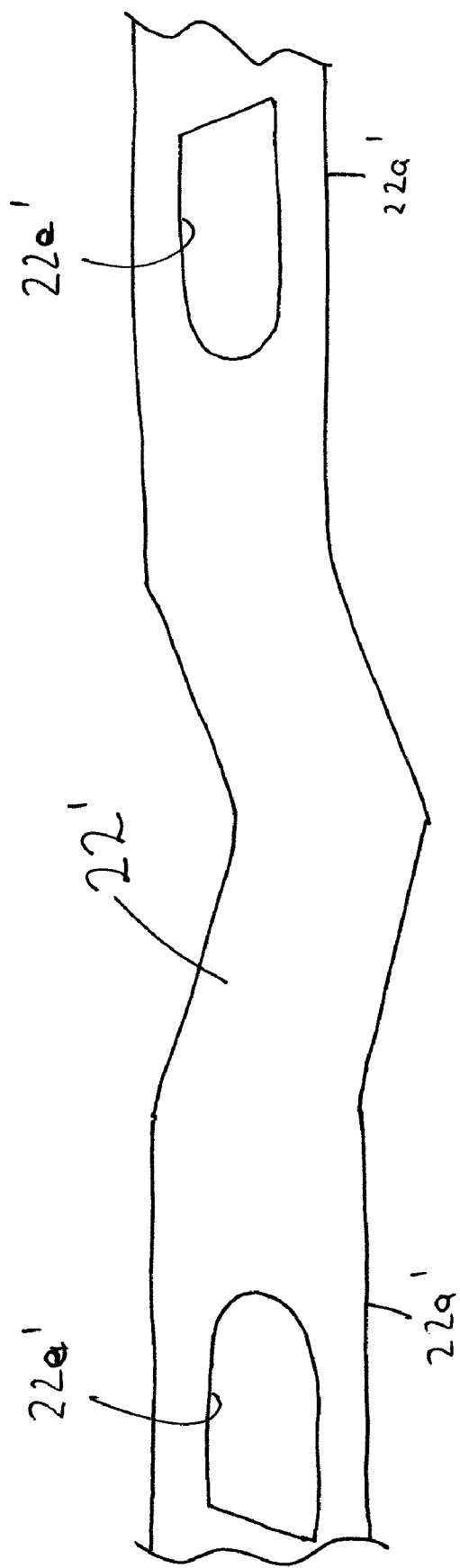
FIG. 12 is a plan view of the fastener of FIGS. 10 and 11, before being formed into a U-shaped clip.
Figure 13:
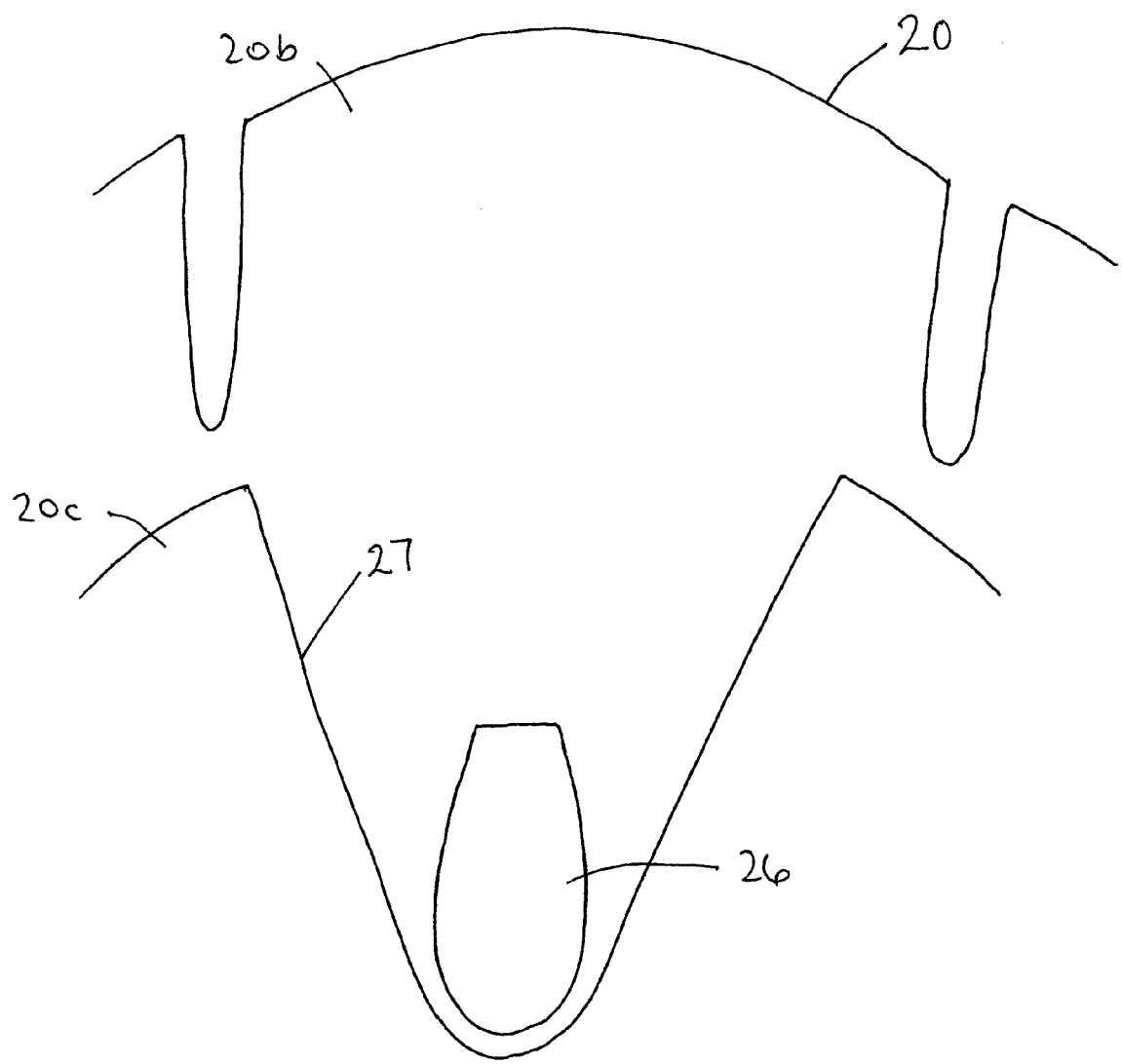
FIGS. 13 and 14 are front and perspective details of a flexible tab or post on the core of FIGS. 7 and 8 for securing a clip fastener to the core.
Figure 14:
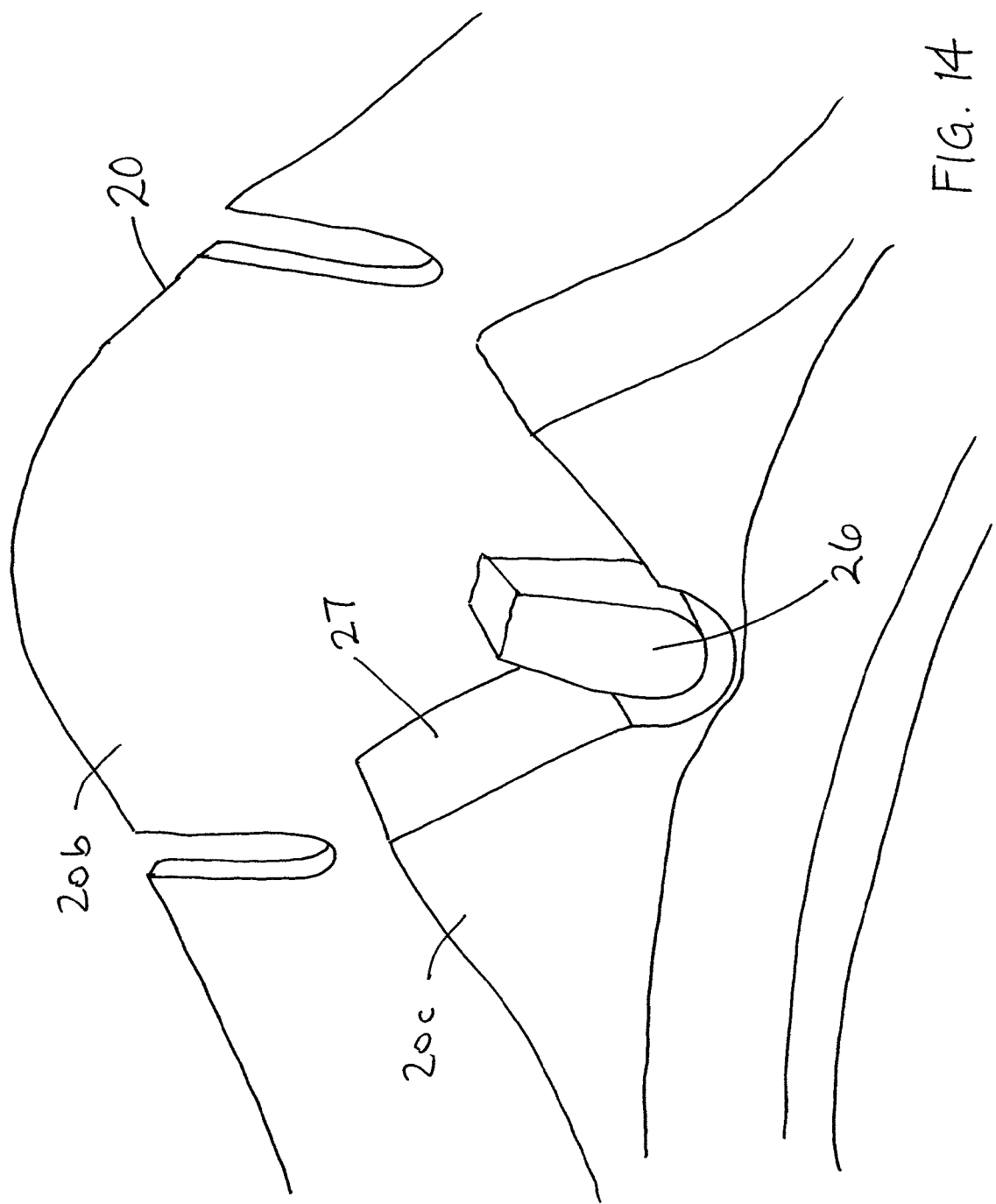

Turning to FIG. 12, each fastener 22' may be formed from a flat sheet of material, e.g., Nitinol or other elastic or superelastic material. For example, the legs 22a' and/or holes 22e' may be stamped, die-cut, laser cut, machined, or otherwise formed from the flat sheet. The legs 22a' may then be bent, roll formed, or otherwise formed into the desired shape, such as that shown in FIGS. 10 and 11.

The fasteners 22 may be embedded, molded, press-fit, or otherwise secured to the gasket member 12. In one embodiment, shown in FIGS. 7, 8, 13, and 14, the gasket member 12 may include a plurality of alignment members or supports 26 onto which the fasteners 22' may be mounted. As shown in FIG. 8, the supports 26 may support the fasteners 22' in a substantially vertical orientation.

The supports 26 may include a post, groove, or the like, e.g., attached to or formed from the core 20a of the cuff 20. For example, as shown in FIGS. 7 and 8, the core 20a may include an upper, relatively thin region 20b and a lower, relatively thick region 20c. These regions 20b, 20c may be provided to provide different flexibility regions in the cuff 20 and/or to enhance sealing between the valve member 14 and gasket member 12, e.g., as described in application Ser. No. 11/069,081, incorporated by reference herein. The supports 26 may be integrally formed when the core 20a is molded, cast, or otherwise formed. Alternatively, the supports 26 may be cut or otherwise formed by removing portions of the lower region 20c, e.g., after molding or otherwise forming the core 20a. In a further alternative, the supports 26 may be attached to the core 20a, e.g., by bonding, sonic welding, using fasteners embedded or inserted through the core 20a, and the like.

Optionally, as shown in FIGS. 7, 8, 13, and 14, tapered channels 27 may be provided above and/or adjacent the supports 26, e.g., formed in the material of the core 20a. For example, the channels 27 may be created when the core 20a is molded or may be created by removing material from the core 20a, e.g., when the supports 26 are formed. The channels 27 may also guide an engagement member 24 (not shown) toward the fastener 22 mounted to the alignment member 26, as explained further below.

Figure 5:
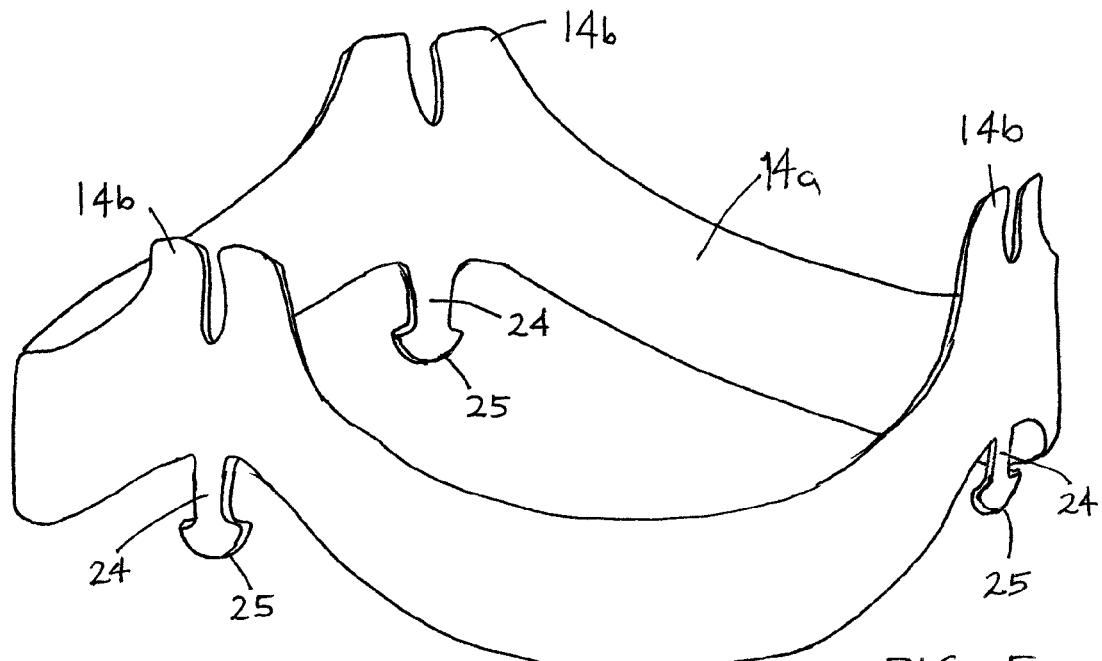
FIGS. 5 and 6 are perspective views of a frame for a valve member, shown before and after being covered with cloth, respectively.
Figure 6:
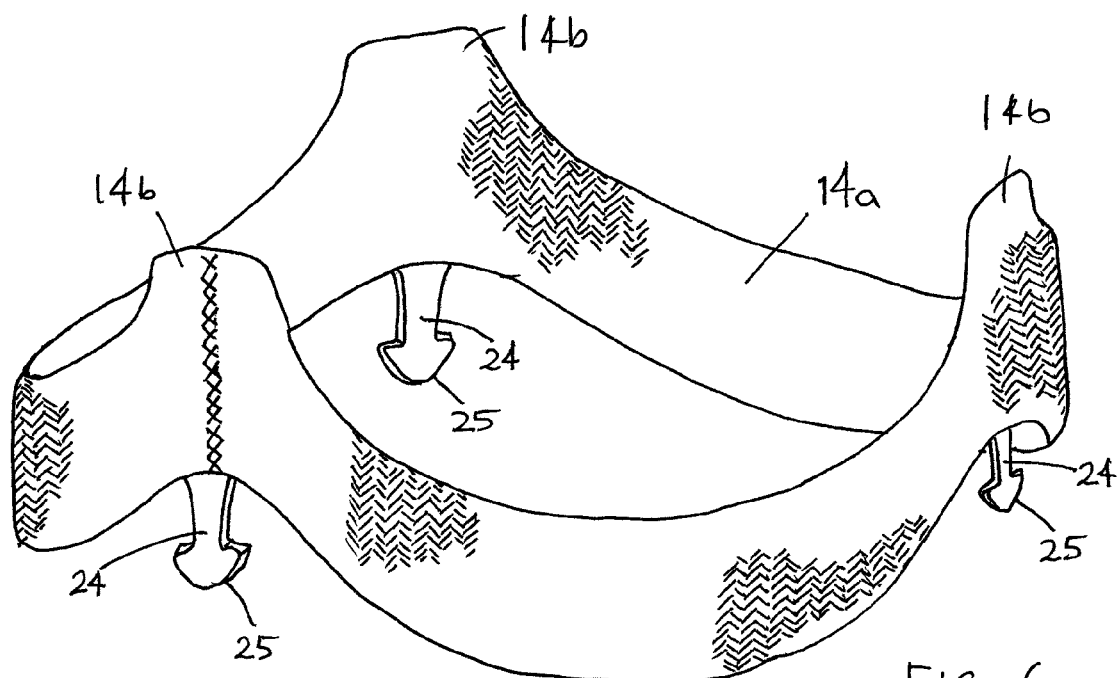

Turning to FIGS. 2, 5, and 6 an exemplary embodiment of the valve member 14 is shown that generally includes a frame 14a carrying a plurality of leaflets 33 or other valve elements (shown in FIG. 2). Turning to FIG. 5, the frame 14a may be formed from substantially rigid or semi-rigid materials, e.g., Nitinol, Elgiloy, stainless steel, plastic, composites, and the like. For example, the frame 14a may be formed from a sheet of Nitinol that is laser cut, stamped, die-cut, or otherwise formed to define the features of the frame 14a frame, e.g., the engagement members 24, commissures 14b, and/or one or more holes or other openings. The frame 14a may be rolled or otherwise formed into an annular shape, e.g., with the ends of the frame 14a attached to one another, e.g., by welding, bonding, fasteners, cooperating connectors, and the like. As shown in FIG. 6, the frame 14a may be substantially covered with cloth, e.g., leaving the engagement members 24 exposed (i.e., without a cloth covering).

As shown in FIG. 2, a plurality of leaflets 33 may be carried by the frame 14a. For example, the leaflets 33 may be tissue leaflets supported by laminate structures (not shown) attached to the frame 14a, such as those disclosed in U.S. Pat. No. 6,371,983 and co-pending application Ser. No. 11/144,254, filed Jun. 3, 2005, the entire disclosures of which are expressly incorporated by reference herein. Alternatively, other valve prostheses may be provided with the engagement member 24, such as mechanical valves, instead of those disclosed Turning to FIG. 9, an exemplary embodiment of an engagement member 24 is shown that may be provided on the frame 14a and/or valve member 14. Generally, the engagement member 24 includes a first end attached or extending from the frame 14a and a second end formed in the shape of a protruding latch or barbed protrusion 25. As shown in FIGS. 5 and 6, the engagement members 24 generally projects downward direction, e.g., substantially vertically from a horizontal plane of the valve member 14. Further, as shown in FIGS. 2 and 3, the engagement members 24 are oriented on the valve member 14 to correspond with their respective mating fasteners 22 in the gasket member 12.

Figure 9:
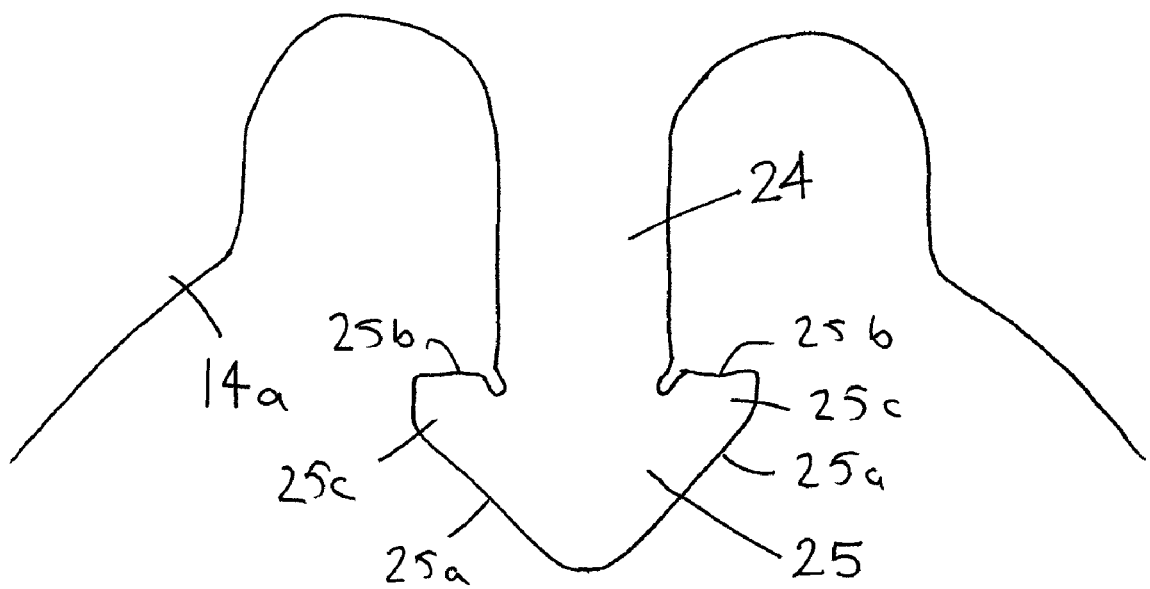
FIG. 9 is a detail of a fastener that may be provided on a frame of a valve member.

Returning to FIG. 9, each engagement member 24 may be formed with a distal head or tip 25 defining one or more tapered first or distal edges 25a and blunt second or proximal edges 25b defining respective tabs or detents 25c. The heads 25 may be formed in the shape of arrows, as shown in FIG. 9, or, alternatively as rounded heads 25, as shown in FIG. 5. As shown in FIGS. 2A-2C and described further below, the heads 25 may be designed to guide or otherwise facilitate inserting the engagement members 24 into the respective fasteners 22, e.g., such that the heads 25 enter the pockets 22c and/or the detents 25c are received in or otherwise engage the hole(s) 22e in the legs 22a of the fasteners 22. In this regard, when the engagement members 24 are inserted into the fasteners 22, the distal heads or tips 25 are locked in position with respect to the fasteners 22, thereby substantially securing the valve member 14 to the gasket member 12.

For example, FIGS. 2A-2C are a series of drawings depicting a single engagement member 24 being inserted into a corresponding fastener 22. As shown in FIG. 2A and explained above, the fastener 22 is a clip that includes a pair of spaced-apart legs 22a defining a funnel-shaped opening 22b and a pocket 22c. As shown in FIG. 2A, the engagement member 24 may be directed towards the fastener 22, e.g., as the valve member 14 is being directed towards the gasket member 12 (not shown; see, e.g., FIG. 3).

The funnel-shaped ends 22d of the legs 22a may facilitate guiding the head 25 of the engagement member 24 into the fastener 22, e.g., by providing a tapering surface for directing the engagement member 24 into fastener 22 even if slightly misaligned. In addition or alternatively, the tapered or rounded distal edges 25a of the head 25 may also guide the head 25 into the opening 22b. As shown in FIG. 2B, the legs 22a of the fastener 22 may spread apart slightly as the engagement member 24 is inserted into the opening 22b. Once the head 25 of the engagement member 24 is pushed further into the fastener 22, i.e., into the pocket 22c, the detents 25c may be aligned with the holes 22e in the legs 22a. Because of the inward bias of the legs 22a of the fastener, the legs 22a may resiliently collapse back, thereby locking the engagement member 24 within the fastener 22.

Figure 15:
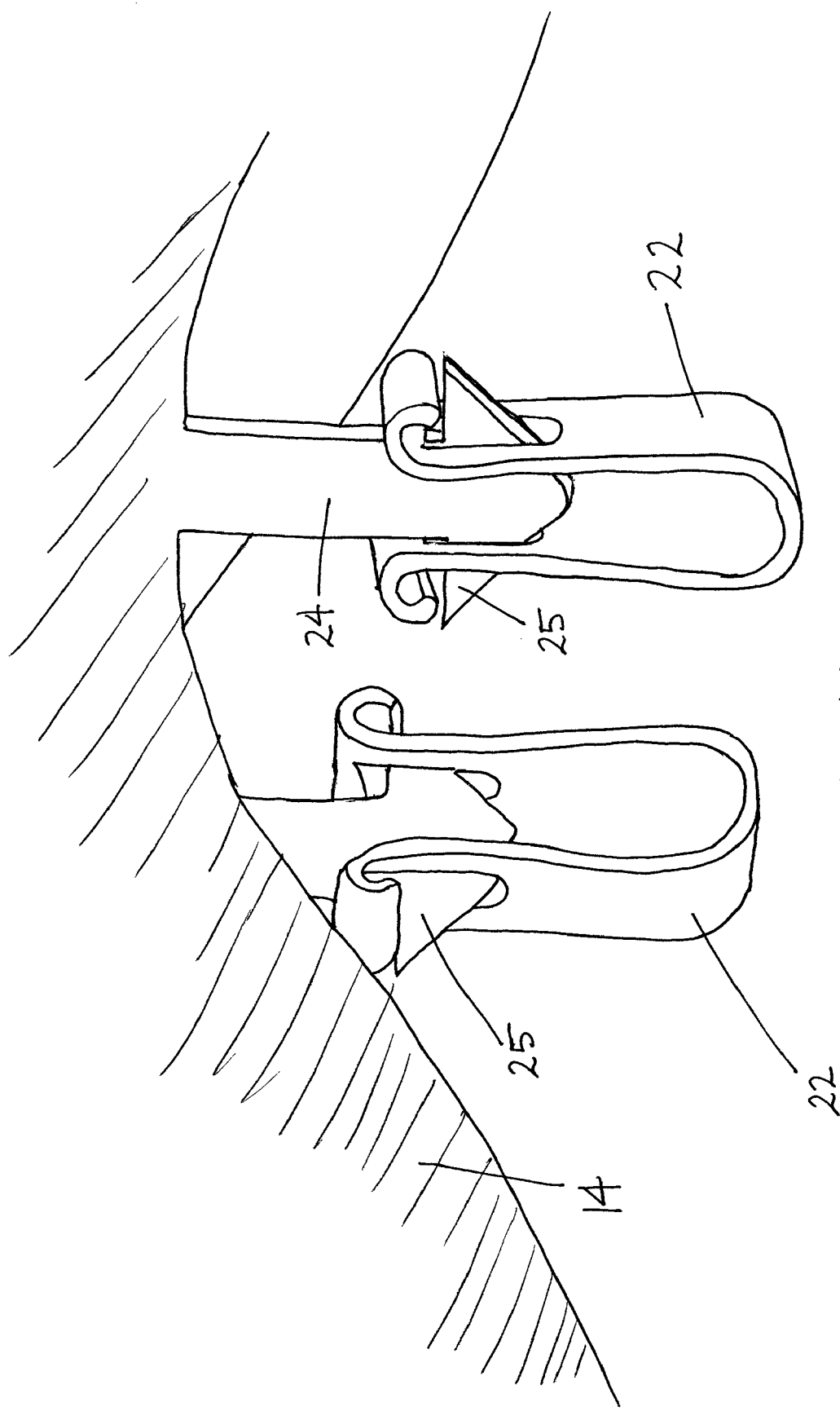
FIG. 15 is a perspective detail of a valve member including fasteners engaged with corresponding fasteners for a gasket member.

In one embodiment, a "snap-fit" is created between the valve member 14 and gasket member 12. The blunt proximal edges 25b of the engagement members 24 prevent removal of the head 25 from the pocket 22c, thereby preventing removal or disengagement of the engagement members 24 from the fasteners 22. In addition, feedback in the form of an audible "click" or tactile "click" may be experienced when the valve member 14 is snapped into the gasket member 12, e.g., as each of the engagement members 24 is engaged with the respective fasteners 22, which may facilitate confirmation that the engagement members 24 are secured within the fasteners 22. FIGS. 3 and 15 also show the valve member 14 secured to the gasket member 12 when the engagement members 24 are engaged with the gasket member 12.

FIG. 3 illustrates an assembled heart valve assembly 10 once the valve member 14 is secured to the gasket member 12, e.g., using three fasteners 22 and corresponding engagement members 24. FIG. 3 also illustrates a clip or fastener passing through the sewing cuff 20, which may be penetrated into surrounding tissue to secure the gasket member 12, as disclosed in co-pending application Ser. Nos. 10/681,700, filed Oct. 8, 2003 and 11/004,445, filed December, 2004. The entire disclosures of these application are expressly incorporated by reference herein.

During use, the heart valve assembly 10 shown in FIGS. 1-3 may be implanted within a patient's body, e.g., within or adjacent to a biological annulus (not shown). The biological annulus may be the site for replacing an existing natural or previously implanted heart valve, such as a tricuspid, mitral, aortic, or pulmonary valve within a patient's heart (not shown).

Before implanting the heart valve assembly 10, the patient may be prepared for the procedure using known methods. For example, the patient may be placed on cardiopulmonary bypass (CPB), and the patient's heart may be exposed, e.g., by sternotomy, thoracotomy, or other open or minimally invasive procedure. An incision may be created in the blood vessel above the valve being replaced (not shown), e.g., the aorta for an aortic valve replacement, in order to access the annulus 90. The existing natural or prosthetic heart valve and/or leaflets (also not shown) may then be removed from the annulus 90 using known methods.

A heart valve assembly 10, including a gasket member 12 and a valve member 14 may be selected based upon the anatomy encountered, e.g., having a plurality of lobes, matching the lobes of the biological annulus and/or having a cross-sectional dimension corresponding to the interior cross-section of the biological annulus. Optionally, a gasket member 12 and/or valve member 14 may selected having a size that is larger than the biological annulus. For example, the gasket member 12 may have a diameter in its relaxed condition that is slightly larger than the biological annulus, e.g., such that the gasket member 12 may at least partially dilate the biological annulus upon implantation. In addition or alternatively, the valve member 14 may have a diameter or other cross-section that is substantially larger than the biological annulus, e.g., for supra-annular or intra-sinus implantation, which may accommodate the larger size.

The gasket member 12 may be introduced into the patient's body and advanced into the biological annulus, e.g., using a delivery tool (not shown). The gasket member 12 may be advanced until the annular ring 18 extends at least partially into the biological annulus. In one embodiment, the annular ring 18 may extend through the biological annulus, i.e., with a lower edge of the annular ring 18 disposed within the sub-annular space below the biological annulus. Optionally, the gasket member 12 may include a flexible skirt (not shown) that may surround and/or extend from the annular ring 18 through the biological annulus. The skirt may be biased to extend outwardly to provide a smooth transition and/or enhance a seal between the gasket member 12 and the biological annulus.

Optionally, the gasket member 12 may then be expanded or at least partially released within the biological annulus, e.g., to dilate tissue surrounding the biological annulus or otherwise direct the surrounding tissue outwardly. With the annular ring 18 deployed within the biological annulus, the sewing cuff 20 may contact the tissue surrounding the supra-annular space above the biological annulus. One or more fasteners (such as fastener 96 shown in FIG. 3), e.g., clips or sutures, may be directed through the gasket member 12 into the tissue above and/or surrounding the biological annulus.

With the gasket member 12 secured within the biological annulus, the valve member 14 may then be advanced into the patient's body towards the biological annulus. The valve member 14 may be oriented to align the commissures 14b with the commissures within the biological annulus, and/or to align the engagement members 24 with the fasteners 22. Optionally, the valve member 14 and/or gasket member 12 may include markers and the like (not shown) to facilitate properly orienting the valve member 14. Exemplary markers and methods for using them are disclosed in co-pending application Ser. No. 10/765,725, filed Jan. 26, 2004, the entire disclosure of which is expressly incorporated by reference herein. Alternatively, the gasket member 12 may include guide rails or members (not shown) over which the valve member 14 may be advanced, such as those disclosed in application Ser. No. 10/765,725 or application Ser. No. 60/748,639, filed Dec. 7, 2005, the entire disclosure of which is also expressly incorporated by reference herein. In this alternative, the engagement members 24 may include holes, passages, or other features (not shown) for slidably receiving the guide members therethrough.

As described above, the engagement members 24 may then be engaged with the respective fasteners 22. For example, the valve member 14 may be tilted slightly to engage a first of the engagement members 24 with the respective fastener 22. The valve member 14 may then be tilted to successively engage each of the other sets of engagements members 24 and fasteners 22. Alternatively, the valve member 14 may be advanced such that the engagement members 24 and fasteners 22 engage substantially simultaneously. If guide members are used, the guide members may be cut, broken, or otherwise severed to allow their removal. Any tools may be removed, leaving the assembled heart valve assembly 10 within the biological annulus.

It will be appreciated that elements or components shown with any embodiment herein are exemplary for the specific embodiment and may be used on or in combination with other embodiments disclosed herein. It will also be appreciated that components, e.g., the fasteners 22 and/or engagement members 24, may be interchanged, provided on either of the gasket member 12 and valve member 14, yet still allow the valve member 12 to be secured to the gasket member 14.

While embodiments of the present invention have been shown and described, various modifications may be made without departing from the scope of the present invention. The invention, therefore, should not be limited, except to the following claims, and their equivalents.

We claim:

1. A prosthesis for receiving a valve prosthesis, comprising:

an annular member advanceable into a tissue annulus;

a sewing cuff extending radially from the annular member; and a plurality of receivers secured to the sewing cuff, each receiver comprising a pair of legs defining a pocket, the legs being deflectable away from one another to accommodate receiving an engagement member from a valve prosthesis in the pocket, the legs being resiliently deflectable towards one another after an engagement member is received in the pocket for securing the engagement member to the receiver, wherein each receiver comprises at least one hole extending through a leg of the receiver to receive a portion of an engagement member therein.

2. The prosthesis of claim 1, wherein the sewing cuff comprises a core to which the receivers are secured, the sewing cuff further comprising a layer of fabric overlying the core.

3. The prosthesis of claim 2, wherein the layer of fabric comprises an opening overlying each receiver for receiving an engagement member therethrough.

4. A prosthetic heart valve, comprising:

a gasket member comprising an annular member advanceable into a tissue annulus, and a sewing cuff extending radially from the annular member;

a valve member comprising a frame carrying a plurality of valve elements;

a plurality engagement members extending from one of the gasket member and the valve member; and a plurality of receivers on the other of the gasket member and the valve member, each receiver comprising a pair of legs defining a pocket, the legs being deflectable away from one another to accommodate receiving a respective engagement member in the pocket, the legs being resiliently deflectable towards one another after the engagement member is received in the pocket for securing the engagement member to the receiver, thereby securing the valve member relative to the gasket member, wherein each engagement member comprises at least one detent, and each receiver comprises at least one hole extending through a leg for receiving the respective detent therein when the engagement member is received in the pocket.

5. The prosthetic heart valve of claim 4, wherein the engagement members extend from the frame of the valve member, and the receivers are attached to the gasket member.

6. The prosthetic heart valve of claim 4, wherein the engagement members are integrally formed with the frame.

7. The prosthetic heart valve of claim 4, wherein each engagement element comprises a tapered or rounded first edge to guide the engagement element into the respective pocket, and a substantially blunt second edge to prevent the engagement element from being removed subsequently from the respective pocket.

8. The prosthetic heart valve of claim 7, wherein each engagement element comprises a pair of detents including tapered or rounded first edges and substantially blunt second edges.

9. The prosthetic heart valve of claim 8, wherein the detents are disposed opposite one another on the engagement element.

10. A method for implanting a prosthetic valve within a biological annulus within a patient's body, the prosthetic valve comprising a gasket member including an annular ring advanceable into a tissue annulus and a sewing cuff extending radially from the annular ring, and a valve member comprising a frame carrying a plurality of valve elements, the method comprising:

introducing the gasket member into the biological annulus such that the annular ring is disposed within the biological annulus and the sewing cuff is disposed supra-annularly above the biological annulus;

securing the gasket member relative to the biological annulus;

after securing the gasket member, introducing the valve member into the patient's body toward the biological annulus; and securing the valve member relative to the gasket member by engaging a plurality of engagement members extending from one of the gasket member and the valve member to a plurality of receptacles on the other of the gasket member and the valve member, each engagement member comprising one or more tabs including tapered first edges and substantially blunt second edges, each receptacle comprising a pocket for receiving a respective engagement member therein and one or more tapered surfaces for guiding a respective engagement member into the receptacle, the substantially blunt second edges preventing removal of the engagement member from the receptacle.

11. The method of claim 10, wherein the gasket member is introduced into the patient's body in a radially compressed configuration, the method further comprising expanding the gasket member such that the annular ring to direct tissue surrounding the biological annulus radially outwardly.

12. The method of claim 10, wherein the frame of the valve member has a multiple lobed shape, and wherein the valve member is oriented within the patient's body to align the engagement members with the receptacles.

* * * * *